(12) United States Patent
Bahler et al.

(10) Patent No.: US 7,659,090 B2
(45) Date of Patent: Feb. 9, 2010

(54) METHODS FOR THE SEPARATION OF STREPTOCOCCUS PNEUMONIAE TYPE 3 POLYSACCHARIDES

(75) Inventors: Brian Douglas Bahler, Apex, NC (US); Erik Heller Hughes, Raleigh, NC (US); Tsu-shun Lee, Irvine, CA (US)

(73) Assignee: Wyeth LLC, Madison, NJ (US)

( * ) Notice: Subject to any disclaimer, the term of this patent is extended or adjusted under 35 U.S.C. 154(b) by 0 days.

(21) Appl. No.: 11/869,206

(22) Filed: Oct. 9, 2007

(65) Prior Publication Data

US 2008/0102498 A1 May 1, 2008

Related U.S. Application Data

(60) Provisional application No. 60/850,665, filed on Oct. 10, 2006.

(51) Int. Cl.
*C12P 1/00* (2006.01)
*A61K 39/38* (2006.01)
*A61K 39/02* (2006.01)

(52) U.S. Cl. .................. 435/41; 424/184.1; 424/234.1; 424/244.1; 424/831; 435/72; 435/101

(58) Field of Classification Search .............. 424/184.1, 424/234.1, 244.1, 831; 435/41, 72, 101
See application file for complete search history.

(56) References Cited

U.S. PATENT DOCUMENTS

2006/0228381 A1  10/2006  Bahler et al.

OTHER PUBLICATIONS

International Search Report dated Apr. 9, 2008 for Intl. App. No. PCT/US207/080768.

*Primary Examiner*—Rodney P. Swartz
(74) *Attorney, Agent, or Firm*—Joseph E. Zahner

(57) ABSTRACT

The present invention provides improved methods for the reduction or removal of protein impurities from a complex cellular *Streptococcus pneumoniae* lysate or centrate comprising serotype 3 polysaccharides involving steps relating to post-lysis heating or pH adjustment. In certain methods, the lysate is heated for a time and at a temperature sufficient to denature proteins present in the lysate and cause their aggregation and precipitation. In one embodiment, the lysate is heated to at least 60° C. for at least 30 minutes to cause protein aggregation and precipitation, more particularly about 60° C. to about 70° C. for about 30 to about 50 minutes, and even more particularly about 65° C. for about 40 minutes. In other methods, the pH of the lysate or centrate is increased to at least 8.0 to improve filterability, more particularly about 8.0 to 8.4, and even more particularly about 8.2. In further methods, heating and pH adjustment steps are combined to cause the aggregation and precipitation of proteins as well as to improve filterability of the lysates or centrates. In other methods, the pH of the lysate or centrate is lowered to about 3.0 to about 5.0 to cause protein aggregation and precipitation. Such methods allow for the production of substantially purified serotype 3 polysaccharide-containing lysates or centrates.

14 Claims, 8 Drawing Sheets

IPPPN3-007

IPPPN3-011

METHODS FOR THE SEPARATION OF STREPTOCOCCUS PNEUMONIAE TYPE 3 POLYSACCHARIDES

CROSS-REFERENCE TO RELATED APPLICATIONS

This application claims the benefit of U.S. Provisional Application No. 60/850,665, filed Oct. 10, 2006, which is incorporated herein in its entirety.

FIELD OF THE INVENTION0

The invention relates to improved methods for the reduction or removal of protein impurities from a complex cellular Streptococcus pneumoniae lysate or centrate comprising serotype 3 polysaccharides involving heating or pH adjustment steps.

BACKGROUND

In the preparation of multivalent conjugate pneumococcal vaccines directed to the prevention of invasive diseases caused by the organism Streptococcus pneumoniae (also known as pneumococcus), selected Streptococcus pneumoniae serotypes are grown to supply polysaccharides needed to produce the vaccine. The cells are grown in large fermentors with lysis induced at the end of the fermentation by addition of sodium deoxycholate (DOC) or an alternate lysing agent. The lysate broth is then harvested for downstream purification and the recovery of the capsular polysaccharide which surrounds the bacterial cells. After conjugation with a carrier protein, the polysaccharide is included in the final vaccine product and confers immunity in the vaccine's target population to the selected Streptococcus pneumoniae serotypes.

Although the cellular lysate produced in this process contains the target polysaccharide, it also contains large quantities of cellular debris including DNA, RNA, proteins, and residual media components. Traditional processing has involved a minimal pH reduction of the lysate to 6.6 by addition of acetic acid to help precipitate out the lysing agent and some of the impurities. This material is subjected to centrifugation followed by filtration to remove most of the solids down to a 0.45 µm nominal size. However, such traditional processing methods have shown minimal reduction in impurities with subsequent difficulty in removing soluble proteins to meet purified polysaccharide specifications.

The high burden of contaminating soluble protein has been particularly problematic within runs for certain serotypes. Some serotypes, in particular Streptococcus pneumoniae Type 3, produce large and viscous polysaccharide chains (e.g., for Type 3, chains of glucose/glucuronic acid of 2-3 million Daltons) that are released into the growth medium upon cellular lysis. Its viscosity has made it difficult to filter after centrifugation, and, in such cases, protein removal through the purification process has been insufficient and has led to run failures.

Accordingly, improved methods for the removal of protein impurities from complex cellular Streptococcus pneumoniae lysates, in particular lysates comprising Streptococcus pneumoniae Type 3 polysaccharides, are needed.

BRIEF SUMMARY OF THE INVENTION

Improved methods for the reduction or removal of protein impurities from a complex cellular Streptococcus pneumoniae lysate or centrate comprising serotype 3 polysaccharides are provided. In one method, a cellular Streptococcus pneumoniae lysate comprising serotype 3 polysaccharides is heated for a time and at a temperature sufficient to denature proteins present in the lysate and cause their aggregation and precipitation. Accordingly, in one embodiment of the invention, the method comprises the steps of: 1) heating the lysate to at least 60° C. for at least 30 minutes to cause protein aggregation and precipitation; and 2) separating precipitants from the lysate; where a substantially purified serotype 3 polysaccharide-containing lysate is produced. In a particular embodiment, the lysate is heated to about 60° C. to about 70° C. for about 30 to about 50 minutes. In another particular embodiment, the lysate is heated to about 65° C. for about 40 minutes. In a further embodiment, the separation step comprises filtering the lysate to remove precipitants using a membrane filter, particularly a 0.45 µm pore size membrane filter. In another embodiment, the separation step comprises filtering the lysate to remove precipitants using a depth filter. In another particular embodiment, the step of separating precipitants from the lysate comprises centrifuging the lysate to remove precipitants.

In another embodiment of the present invention, a method is provided for reducing or removing protein impurities from a cellular Streptococcus pneumoniae lysate or centrate comprising serotype 3 polysaccharides that comprises a step involving pH adjustment of the lysate or centrate. In this embodiment, the pH adjustment step improves filterability. In a particular embodiment, the pH of the lysate or centrate is increased to at least 8.0 prior to filtration, particularly to between about 8.0 to about 8.4 prior to filtration, and more particularly to about 8.2 prior to filtration. In a further embodiment, the filtration step comprises filtering the lysate or centrate using a membrane filter, particularly a 0.45 µm pore size membrane filter. In another embodiment, the filtration step comprises filtering the lysate or centrate using a depth filter.

In another embodiment of the present invention, a method is provided for reducing or removing protein impurities from a cellular Streptococcus pneumoniae lysate comprising serotype 3 polysaccharides that comprises a lysate heating step combined with a step involving pH adjustment of the lysate or of a centrate produced by centrifugation of the lysate. In this embodiment, the pH adjustment step improves filterability. Accordingly, in one embodiment the method comprises the steps of: 1) heating the lysate to at least 60° C. for at least 30 minutes to cause protein aggregation and precipitation; 2) centrifuging the lysate and separating precipitated proteins from the lysate to produce a centrate; 3) increasing the pH of the centrate to at least 8.0; and 4) filtering the centrate; where a substantially purified serotype 3 polysaccharide-containing centrate is produced. In a particular embodiment, the lysate is heated to about 60° C. to about 70° C. for about 30 to about 50 minutes prior to centrifugation, more particularly to about 60° C. for about 40 minutes. In another embodiment, the pH of the centrate is increased to between about 8.0 to about 8.4 prior to filtration, particularly about 8.2. In a further embodiment, the filtration step comprises filtering the lysate to remove precipitants using a membrane filter, more particularly a 0.45 µm pore size membrane filter. In another embodiment, the filtration step comprises filtering the lysate to remove precipitants using a depth filter.

In another embodiment of the present invention, a method is provided for reducing or removing protein impurities from a cellular Streptococcus pneumoniae lysate or centrate comprising serotype 3 polysaccharides that comprises a pH adjustment step to cause protein aggregation and precipitation. In this embodiment, the method comprises the steps of:

1) lowering the pH of said lysate to about 3.0 to about 5.0 to cause protein aggregation and precipitation; 2) centrifuging the lysate and separating precipitated proteins from the lysate to produce a centrate; 3) increasing the pH of the centrate to at least 8.0; and 4) filtering the centrate; where a substantially purified serotype 3 polysaccharide-containing centrate is produced. In a particular embodiment, the pH of the lysate is lowered to about 3.0 prior to centrifugation. In another particular embodiment, the pH of the centrate is increased to between about 8.0 to about 8.4 prior to filtration, more particularly about 8.2. In a further embodiment, the pH adjustment step to cause protein aggregation and precipitation further comprises heating the lysate to at least 60° C. for at least 30 minutes, more particularly to about 60° C. to about 70° C. for about 30 to about 50 minutes, and even more particularly to about 60° C. for about 40 minutes. In a further embodiment, the filtration step comprises filtering the lysate to remove precipitants using a membrane filter, more particularly a 0.45 µm pore size membrane filter. In another embodiment, the filtration step comprises filtering the lysate to remove precipitants using a depth filter.

DETAILED DESCRIPTION OF THE INVENTION

Figure 1:
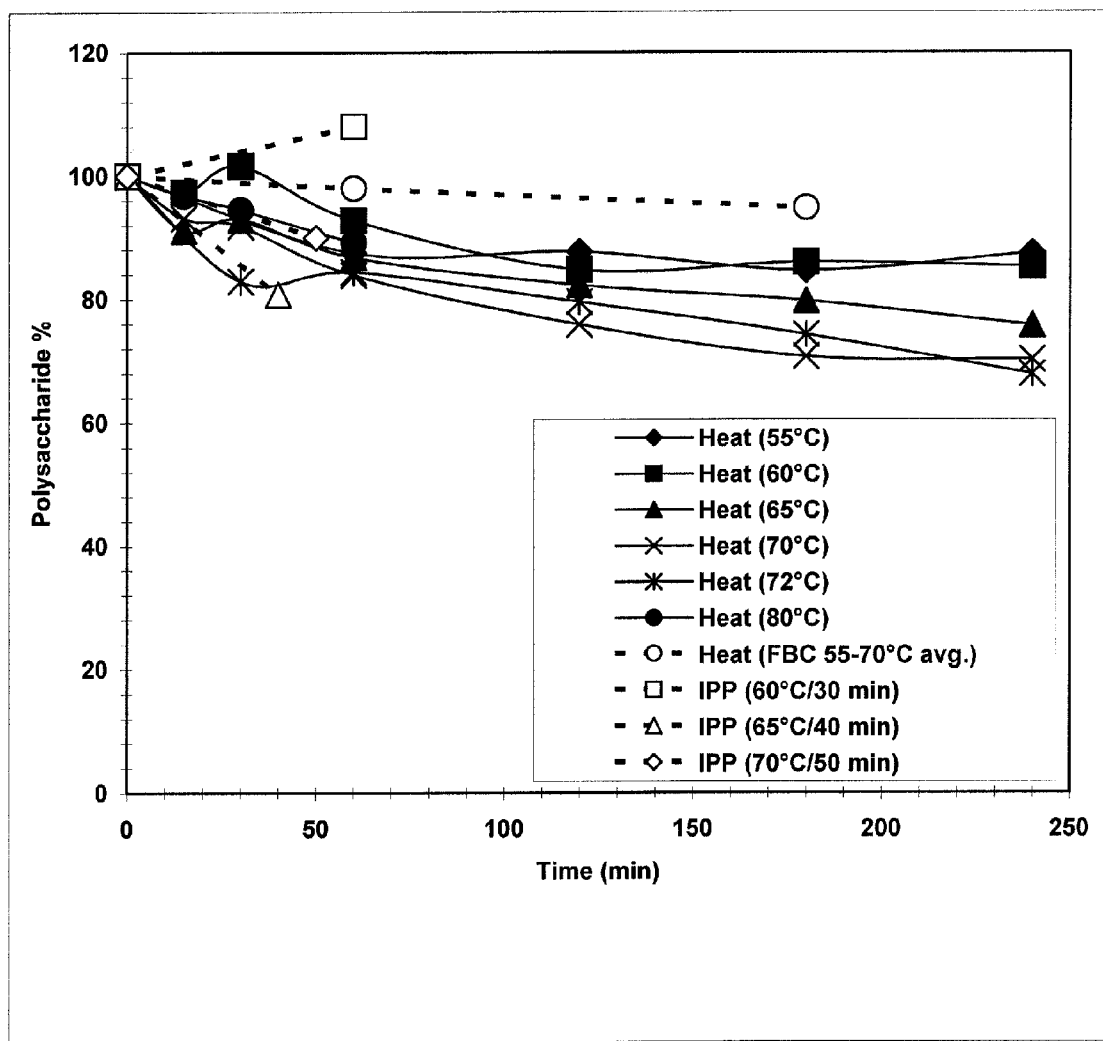
FIG. 1 shows polysaccharide yield from laboratory studies of various heating conditions and holding times for serotype 3 lysates. Data is shown as a percentage of values from unheated process samples to show relative percent protein losses of treated samples (100% is equivalent to no loss).

The present invention provides improved methods for the reduction or removal of protein impurities from a complex cellular *Streptococcus pneumoniae* lysate or centrate comprising serotype 3 polysaccharides involving steps relating to post-lysis heating or pH adjustment. In certain methods, the lysate is heated for a time and at a temperature sufficient to denature proteins present in the lysate and cause their aggregation and precipitation. In other methods, the lysate, or a centrate produced by centrifugation of the lysate, is pH adjusted to improve filterability or cause the aggregation and precipitation of proteins. In further methods, heating and pH adjustment steps are combined to cause the aggregation and precipitation of proteins as well as to improve filterability of the lysates or centrates. Such methods allow for the production of substantially purified serotype 3 polysaccharide-containing lysates or centrates.

As used herein, the term "substantially purified serotype 3 polysaccharide-containing lysate" or "substantially purified serotype 3 polysaccharide-containing centrate" refers to a cellular *Streptococcus pneumoniae* serotype 3 lysate or centrate from which protein has been removed such that the relative protein concentration of the lysate or centrate is less than about 40%, about 35%, about 30%, about 25%, about 20%, about 15%, about 10%, about 5%, or about 1% protein compared to the concentration of protein in the lysate or centrate prior to protein removal. Methods for the quantification of protein concentration in a cellular lysate or centrate are well known in the art and include, for example, sodium dodecyl sulfate polyacrylamide gel electrophoresis (SDS-PAGE) analysis, chromatography, and electrophoresis (See, e.g., Deutscher, M. P. (ed.), *Guide to Protein Purification*, San Diego: Academic Press, Inc. (1990)).

In one embodiment, the present invention provides a method comprising a heating step for the reduction or removal of protein impurities from a cellular *Streptococcus pneumoniae* lysate comprising serotype 3 polysaccharides. Exposure to heat disrupts the native structure of proteins and denatures them without affecting the polysaccharide. Subsequently, denatured proteins aggregate and precipitate, improving lysate separation and enabling easy removal of solids by centrifugation or filtration. Such a heating step would be effective for the recovery or purification of any heat-stable polysaccharide from a biological mixture containing significant levels of soluble protein impurities and therefore may be used in any liquid phase where soluble protein levels remain problematic (for example, biological mixtures comprising DNA, RNA, polysaccharides, oligosaccharides, saccharides, fatty acids, and lipids).

Thus, in one embodiment, the present invention provides a method for the reduction or removal of protein impurities from a cellular *Streptococcus pneumoniae* lysate comprising serotype 3 polysaccharides comprising the steps of: 1) heating the lysate to at least 50° C., at least 55° C., or at least 60° C. for at least 15 or at least 30 minutes to cause protein aggregation and precipitation; and 2) separating precipitants from the lysate; where a substantially purified serotype 3 polysaccharide-containing lysate is produced. In a particular embodiment, the lysate is heated to about 50° C. to about 80° C. for about 15 to about 60 minutes. In another particular embodiment, the lysate is heated to between about 60° C. to about 70° C. for about 30 to about 50 minutes. In another particular embodiment, the lysate is heated to about 65° C. for about 40 minutes. As described in more detail in the Experimental Section below, for heat stable serotype 3 polysaccharides, over 80% of protein has been removed by heating at 65° C. for 40 minutes with minimal losses of polysaccharide. In a further embodiment, the separation step comprises centrifugation or filtration to remove or reduce protein from the lysate. In particular, in one embodiment, the separation step comprises filtering the lysate to remove precipitants using a membrane filter, particularly a 0.45 µm pore size membrane filter. In another embodiment, the separation step comprises filtering the lysate to remove precipitants using a depth filter.

Filters typically used for high volume filtration processes such as the purification of serotype 3 polysaccharides include membrane (or surface) filters and depth filters. Membrane filters function primarily by size exclusion, in which all impurities in a solution to be filtered that are larger than the set pore size of the membrane filter are trapped on the surface of the filter. By contrast, depth filters contain a fibrous or granular matrix with a random porous structure through which a solution to be filtered is passed, and function primarily through random adsorption and mechanical entrapment of impurities throughout the depth of the matrix. Within the methods of the present invention, both membrane and depth filters may be used in combination, with the depth filter collecting larger impurities and the surface filter capturing smaller impurities.

In another embodiment of the present invention, a method is also provided for reducing or removing protein impurities from a cellular *Streptococcus pneumoniae* lysate comprising serotype 3 polysaccharides or of a centrate produced by centrifugation of the lysate comprising a step involving pH adjustment of the lysate or centrate. In this embodiment, the pH adjustment step improves filterability. As used herein, "filterability" of a cellular *Streptococcus pneumoniae* lysate or centrate comprising serotype 3 polysaccharides refers to the ability to pass the lysate or centrate through a filter, such as a membrane or depth filter. Improved filterability of a lysate or centrate is therefore associated with, for example, increased flow rate of the lysate or centrate across a filter, reduced clogging of filters by the lysate or centrate, or reduced pressure required to pass a given volume of lysate or centrate across a filter.

Traditional methods for the removal of impurities from cellular *Streptococcus pneumoniae* lysates or centrates comprising serotype 3 polysaccharides have involved a minimal pH reduction of the lysate to 6.6 by addition of acetic acid followed by continuous centrifugation and filtration down to 0.45 µm. This processing method has shown minimal reduction in impurities with subsequent difficulty in the ability to remove soluble proteins through membrane or depth filters prior to sending the product to purification processing. However, the methods of the present invention relate to the discovery that the filterability of this high molecular weight polysaccharide can be altered as a direct function of pH, and that increasing the pH of a lysate or centrate improves filterability without significant loss in polysaccharide serotype 3 molecular weight size or functionality.

Thus, in one embodiment of the present invention, a method is provided for reducing or removing protein impurities from a cellular *Streptococcus pneumoniae* lysate comprising serotype 3 polysaccharides or of a centrate produced by centrifugation of the lysate that comprises the step of increasing the pH of the centrate or lysate to at least 8.0 prior to filtration. In another embodiment, the pH of the centrate or lysate is increased to about 8.0 to about 8.4 prior to filtration, more particularly about 8.2. Filtration following pH adjustment of the lysate or centrate may involve filtering the lysate or centrate using a membrane filter, particularly a 0.45 µm pore size membrane filter. In another embodiment, filtering the lysate or centrate may involve using a depth filter.

In a further embodiment, a method is provided for reducing or removing protein impurities from a cellular *Streptococcus pneumoniae* lysate comprising serotype 3 polysaccharides that comprises a lysate heating step combined with a step involving pH adjustment of the lysate. In one embodiment, the method comprises the steps of: 1) heating the lysate to at least 50° C., at least 55° C., or at least 60° C. for at least 15 or at least 30 minutes to cause protein aggregation and precipitation; 2) centrifuging the lysate and separating precipitated proteins from the lysate to produce a centrate; 3) increasing the pH of the centrate to at least 8.0; and 4) filtering the centrate; where a substantially purified serotype 3 polysaccharide-containing centrate is produced. In a particular embodiment, the lysate is heated to about 50° C. to about 80° C. for about 15 to about 60 minutes prior to centrifugation. In another particular embodiment, the lysate is heated to about 60° C. to about 70° C. for about 30 to about 50 minutes prior to centrifugation. In a further embodiment, the lysate is heated to about 65° C. for about 40 minutes prior to centrifugation. In another particular embodiment, the pH of the centrate is increased to about 8.0 to about 8.4 prior to filtration, more particularly about 8.2. In a further embodiment, the filtration step involves filtering the centrate using a membrane filter, particularly a 0.45 µm pore size membrane filter. In another embodiment, the filtration step comprises filtering the lysate to remove precipitants using a depth filter.

In a further embodiment, a method is provided for reducing or removing protein impurities from a cellular *Streptococcus pneumoniae* lysate or centrate comprising serotype 3 polysaccharides that comprises a pH adjustment step to cause protein aggregation and precipitation. In one embodiment, the method comprises the steps of: 1) lowering the pH of said lysate to less than about 5.0, 4.5, 4.0, 3.5, or 3.0, or to about 3.0 to about 5.0 to cause protein aggregation and precipitation; 2) centrifuging the lysate and separating precipitated proteins from the lysate to produce a centrate; 3) increasing the pH of the centrate to at least 8.0; and 4) filtering the centrate; where a substantially purified serotype 3 polysaccharide-containing centrate is produced. In a particular embodiment, the pH of the lysate is lowered to about 3.0 prior to centrifugation. In another particular embodiment, the pH of the centrate is increased to between about 8.0 to about 8.4 prior to filtration, more particularly about 8.2. In a particular embodiment, the filtration step comprises filtering the lysate to remove precipitants using a membrane filter, more particularly a 0.45 µm pore size membrane filter. In another embodiment, the filtration step comprises filtering the lysate to remove precipitants using a depth filter.

In a further embodiment, the method for reducing or removing protein impurities from a cellular *Streptococcus pneumoniae* lysate or centrate comprising serotype 3 polysaccharides that comprises a pH adjustment step to cause protein aggregation and precipitation further comprises heating the lysate to at least 50° C., at least 55° C., or at least 60° C. for at least 15 or at least 30 minutes to cause protein aggregation and precipitation. In a particular embodiment, the lysate is heated to about 50° C. to about 80° C. for about 15 to about 60 minutes prior to centrifugation. In another particular embodiment, the lysate is heated to about 60° C. to about 70° C. for about 30 to about 50 minutes prior to centrifugation. In a further embodiment, the lysate is heated to about 65° C. for about 40 minutes prior to centrifugation.

The following examples are offered by way of illustration and not by way of limitation.

EXPERIMENTAL

*Streptococcus pneumoniae* Type 3 produces a very large and viscous polysaccharide which is released into the growth medium upon cellular lysis. This lysis is currently induced with sodium deoxycholate (DOC) at the end of the fermentation. Type 3 polysaccharide appears to be very stable over a wide temperature and pH range; however, its viscosity has made it difficult to filter after centrifugation, which has led to low recovery of cell free broth (CFB). The following examples describe studies relating to post-lysis heating to denature and precipitate out proteins as well as pH adjustment to improve filterability of the lysate.

EXAMPLE 1

Heating Step

Implementing a heating step for *Streptococcus pneumoniae* serotype 3 recovery was driven by a need to decrease the protein load before purification steps. Batches of purified polysaccharide were prone to batch failures due to residual protein levels above the set specification level of 5% w/w protein/polysaccharide. The following laboratory studies were therefore performed to characterize the effectiveness and ranges for use of a heating step in the purification and recovery of *Streptococcus pneumoniae* serotype 3. The goal for including this heating step was to produce a reduction in protein levels while maintaining high polysaccharide levels.

In the laboratory, fermentation cellular lysate material obtained from pilot plant runs was aliquoted into Falcon™ tubes (BD Biosciences, Bedford, Mass.) and heated in water baths to various temperatures. Temperatures studied ranged from 50° C. to 80° C., with hold times from 15 minutes to 240 minutes. Control samples were left at ambient room temperature (about 21° C.). All samples were then held overnight at ambient conditions, after which the samples were centrifuged and run through 0.45 µm syringe filters (HT Tuffryn® Membrane 25 mm syringe filters, low protein binding, Pall Life Sciences, Anne Arbor, Mich.) to provide material for polysaccharide and protein analysis. Experimental data was analyzed by a statistical software package (Cornerstone™ from Applied Systems Technologies, Inc., Dunnellon, Fla.) to identify the impact of temperature and time on polysaccharide and protein levels.

Polysaccharide and Protein Analysis

Polysaccharide analysis was performed by HPLC-SEC (High Performance Liquid Chromatography—Size Exclusion Column) using standard methodology well known in the art (see, e.g., Aquilar, M. "HPLC of Peptides and Proteins: Methods and Protocols" Totowa, N.J.: Humana Press (2004)). FIG. 1 shows polysaccharide yield from laboratory studies of various heating times. Data reported is a percentage of control polysaccharide levels with 100% indicating no loss. As shown in FIG. 1, polysaccharide yields were stable with respect to heating time and temperatures.

Pilot scale data was also collected and is shown in FIG. 1 as data points designated with an "IPP" abbreviation. Listed times reflect heat up, heat hold at designated conditions, and cool down periods. These samples were taken after heat processing in the actual fermentor as opposed to heating in the laboratory. Within the temperature and time ranges tested at pilot scale (30 to 50 minutes and 60° C. to 70° C.) polysaccharide losses ranged from 0-18% with most test losses of 10% or less. This was within an acceptable range for downstream processing of this material.

Protein analysis was performed by using standard SDS-PAGE (Sodium Dodecyl Sulfate Polyacrylamide Gel Electrophoresis) methods well known in the art (see, e.g., Walker, J. M. "The Protein Protocols Handbook" Totowa, N.J.: Humana Press (2002)). Analysis of the gels was performed with the aid of a gel imaging system (UVP Imager with Labworks™ V.3 software, UVP Inc., Upland, Calif.) to interpret total band (lane) densities against a protein standard.

Figure 2:
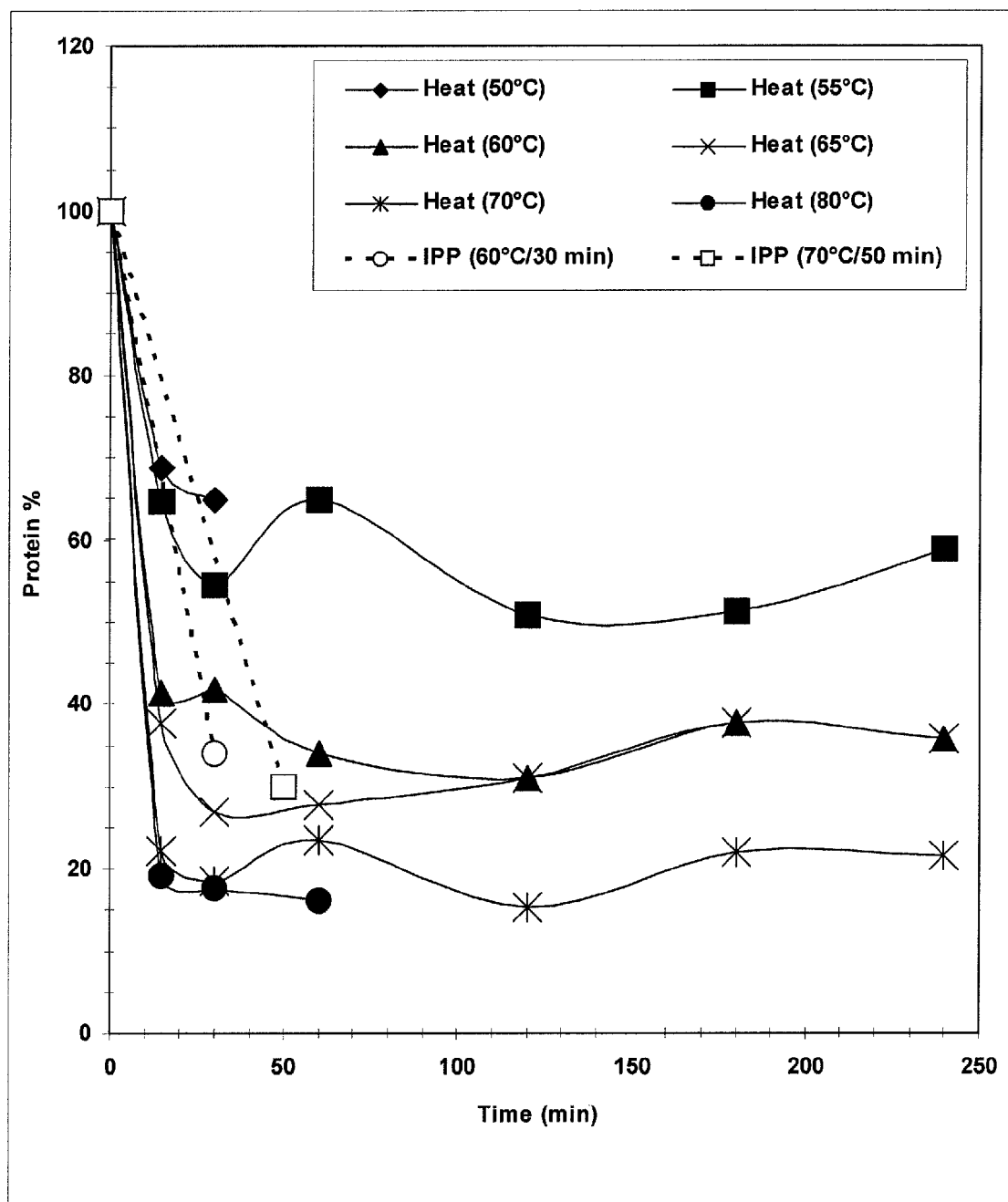
FIG. 2 shows protein yield from laboratory studies of various heating conditions and holding times for serotype 3 lysates. Data is shown as a percentage of values from unheated process samples to show relative percent protein losses of treated samples (100% is equivalent to no loss).

As shown in FIG. 2, temperatures from 50° C. to 80° C. were studied at both laboratory and pilot scale (data points designated with an "IPP" abbreviation). Protein data is shown as a percentage of control values from unheated process samples to show relative percent protein losses of treated samples. Heating times of 15 minutes were adequate to remove 60% of soluble protein through heat precipitation at temperatures of 60° C. (see FIG. 2). While significant protein reduction occurred at 50° C. and 55° C., 60° C. was set as a minimum for pilot plant operation due to more robust levels of protein removal.

Figure 3:
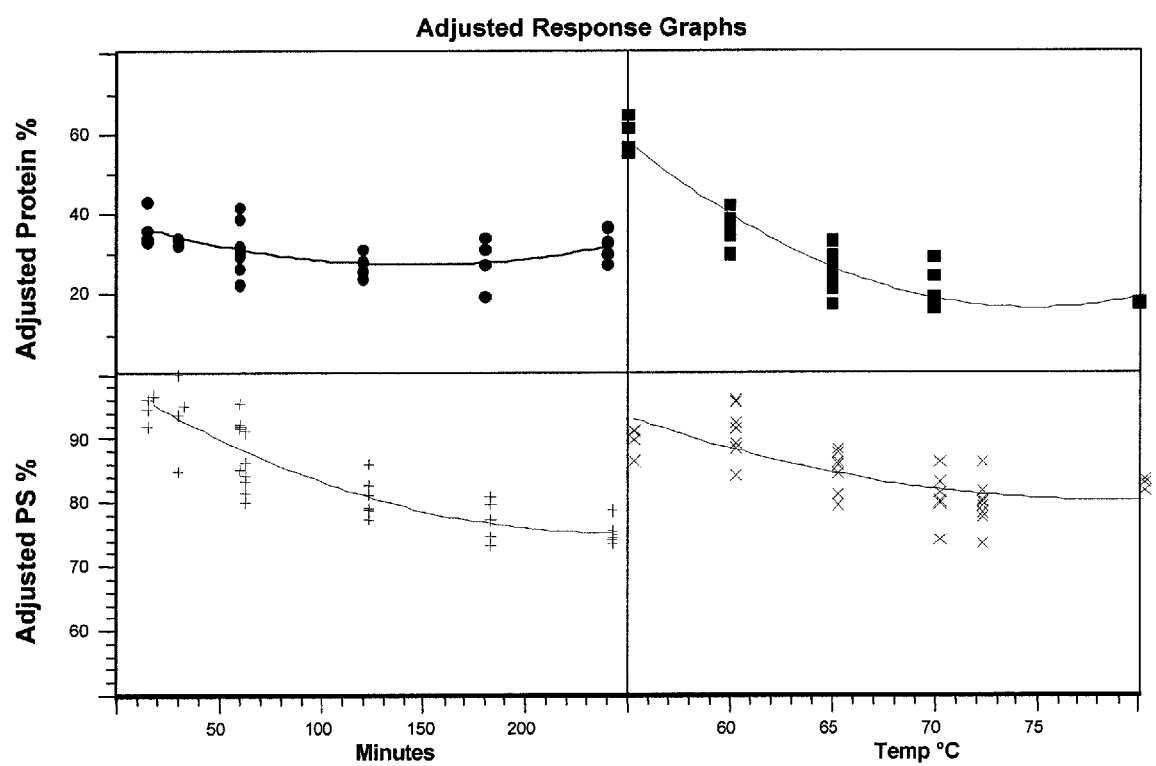
FIG. 3 shows an adjusted response graph of the effects of time (left) and temperature (right) on protein (top) and polysaccharide (PS, bottom) concentrations in serotype 3 lysates. "Adjusted PS %" and "Adjusted Protein %" values represent the percentage of polysaccharide and protein concentrations, respectively, at various time and temperature points as compared to time=0 minutes and room temperature (which represent 100% values for protein and polysaccharide concentrations).

FIG. 3 shows an Adjusted Response Graph of protein and polysaccharide concentration plotted by time and temperature. The data shown represent the percentage of protein and polysaccharide concentrations at various time and temperature points as compared to Time=0 minutes and room temperature (which represent 100% values for protein and polysaccharide). As shown in FIG. 3, hold temperature had a significant impact on soluble protein removal while duration was unimportant beyond a 15 minute hold. For polysaccharide (PS) yield, both time and temperature showed limited impact on PS losses (<20% loss, which is acceptable for downstream processing).

Figure 4:
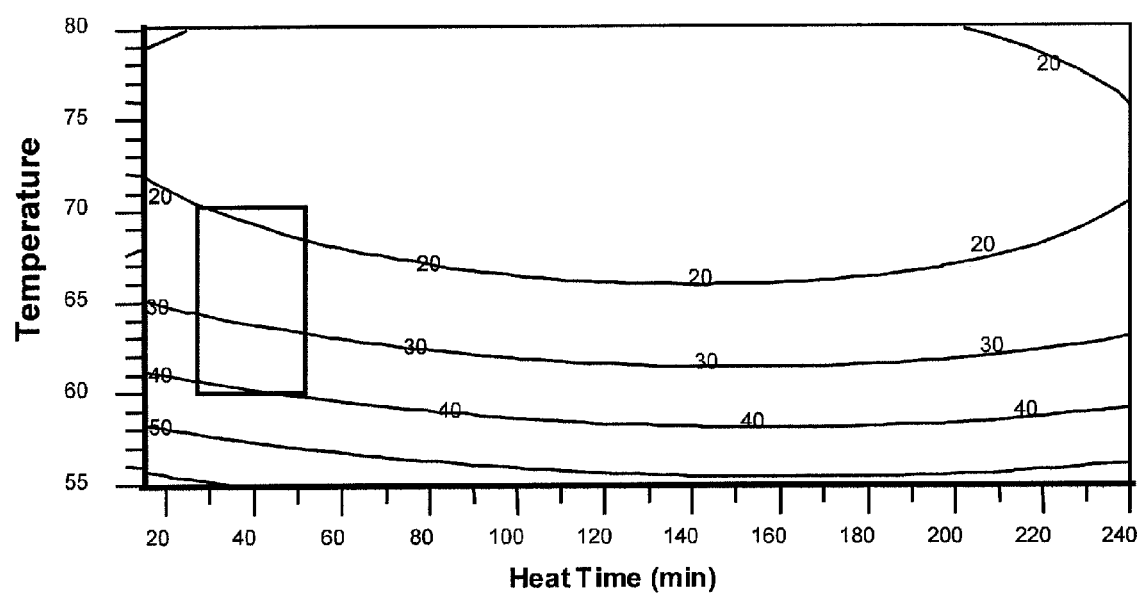
FIG. 4 shows a contour plot of total percent protein from serotype 3 lysates plotted by temperature and time conditions. The percentage of remaining soluble protein is shown in the curved bars on the graph. The range of 60° C.-70° C. for 30-50 minutes is highlighted by a box.

FIG. 4 shows a contour plot of total percent protein from serotype 3 lysates plotted by temperature and time conditions. The percentage of remaining soluble protein is shown in the curved bars on the graph. The range of 60° C.-70° C. for 30-50 minutes is highlighted by a box and represents a preferred range selected for implementation of the heating step described herein. However, as described above, wider ranges were also analyzed and shown to be effective.

Figure 5:
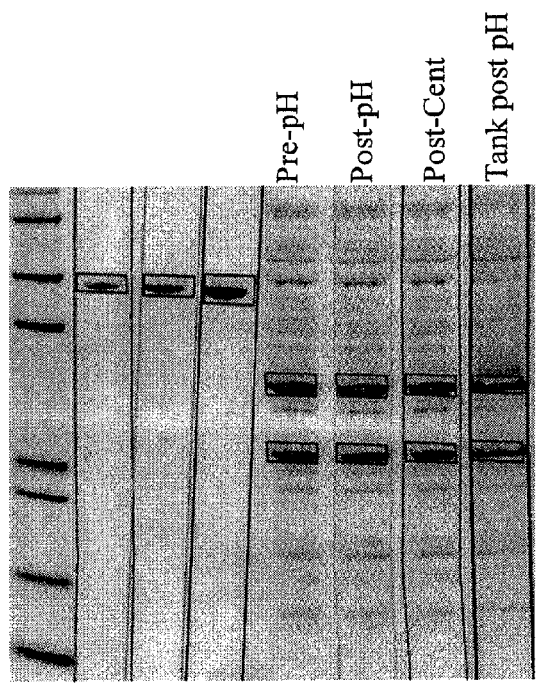
FIG. 5 shows SDS-PAGE gels showing soluble protein removal from heat treated cell lysate. Non-heat treated lanes are on the left (IPPPN3-007) and heat treated lanes are on the right (IPPPN3-011).
Figure 5:
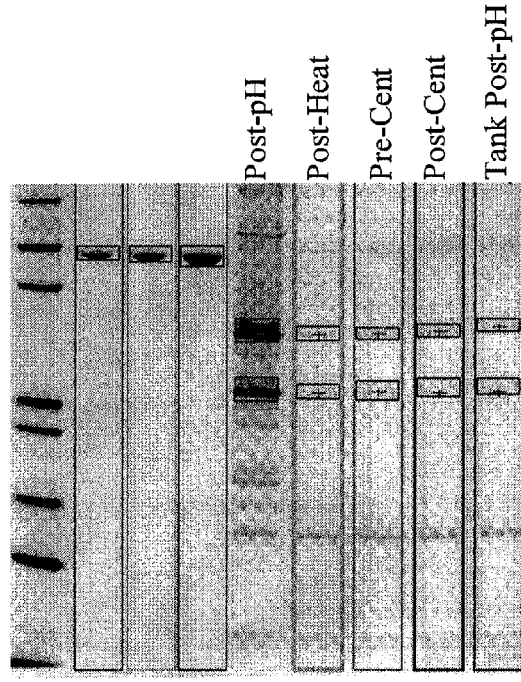

FIG. 5 shows SDS-PAGE gels of soluble protein following testing of the heating step at pilot scale. The gel on the left shows results from a pilot scale fermentation batch (IPPPN3-007) without a heating step and shows intact protein levels throughout the recovery process (pre-pH, Post-pH, Post-Centrifugation, and Tank Post-pH adjustment). "Tank Post-pH adjustment" refers to samples taken from a hold tank for the centrate following adjustment to a given pH level prior to filtration. A 100 kilodalton (KD) tangential flow purification ultrafiltration (UF) process was used to remove solutes smaller than 100 KD by gradually replacing the original suspension medium with a buffered solution using continuous circulation and filtration followed by concentration of the solution. Following this UF process step, the protein content of batch IPPPN3-007 was reported at 31% Protein/Polysaccharide on a w/w basis. Final protein level after the complete purification process was 9.9% (w/w against polysaccharide) resulting in failure of the batch to meet a Final Batch Concentrate (FBC) specification of ≦5% protein. For batch IPPPN3-011, a heating step with a hold of 60° C. for 30 minutes was included after the lysate hold and prior to downstream processing. The protein level after 100 K UF filtration was 6.7%, and the FBC protein level was 2.5%, which passed the FBC drug intermediate specification. As indicated in the gel image in FIG. 5 on the right, the heating step resulted in a significant reduction of protein levels during recovery operations.

A summary of pilot scale data relating to this heating step is also shown in Table 1. Runs -001, -004, -005, -007, and -013 used no heating step. Of these runs, only -001 and -004 passed a target protein specification of ≦5% w/w indicating a continued difficulty of the purification process removing protein loads of 20% to 35% after the UF process step. With the inclusion of a heating hold step as indicated in Table 1 for runs -011, -012, -014, -015, and -017, protein loads were reduced to 3.1% to 6.7% after the UF process step, with final protein levels in the purified polysaccharide of 0.6% to 2.5%.

TABLE 1

Percent Protein Following Ultrafiltration and in Final Batch Concentrate (FBC) for Various Heating Conditions and Hold Times

| Process | Batch | UF Protein % | FBC Protein % |
|---|---|---|---|
| No Heat | IPPPN3-001 | 32 | 4.8 |
| No Heat | IPPPN3-004 | 35 | 3.5 |
| No Heat | IPPPN3-005 | 20 | 7.4 |
| No Heat | IPPPN3-007 | 31 | 9.9 |
| No Heat | IPPPN3-013 | 22 | 6.1 |
| Heat 60° C./30 min | IPPPN3-011 | 6.7 | 2.5 |
| Heat 70° C./50 min | IPPPN3-012 | 4.3 | 1.7 |
| Heat 65° C./40 min | IPPPN3-014 | 3.1 | 0.9 |
| Heat 65° C./40 min | IPPPN3-015 | 3.7 | 0.6 |
| Heat 65° C./40 min | IPPPN3-017 | 3.4 | 1.7 |

Figure 6:
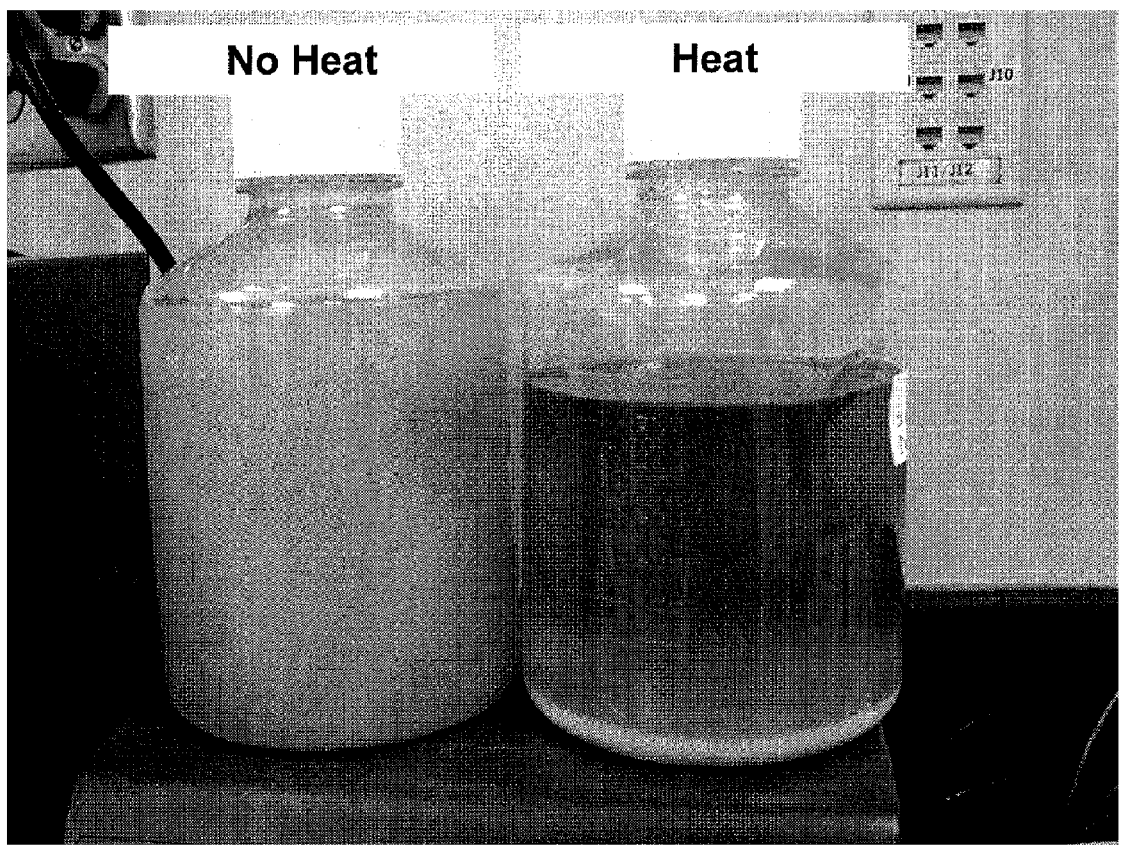
FIG. 6 shows a photograph comparing heat-treated (right) and non-heat treated (left) serotype 3 lysates following identical times for precipitate settling.

The implementation of the heating step also improved separation efficiency by increasing the aggregation of protein which allows for more efficient centrifugation. The effect of this step is illustrated in FIG. 6, in which a photograph provides a comparison of non-heated (left) and heated (right) cellular lysate after an overnight non-agitated hold at ambient conditions. The media was noticeably clearer following heat treatment, reflecting greater aggregation and precipitation of protein.

As shown by the data described above, the inclusion of a heating step was important in removing protein impurities for the production of polysaccharide. Final polysaccharide met drug intermediate release criteria of ≦5% w/w (protein/polysaccharide), demonstrating product stability with regard to heat treatment.

EXAMPLE 2 pH Adjustment and Filtration Step

Traditional filtration for *Streptococcus pneumoniae* polysaccharides included in the Prevnar® vaccine has involved continuous centrifugation of cellular lysates followed by depth filtration and membrane filtration. As described above, *Streptococcus pneumoniae* Type 3 is a large polysaccharide that is viscous in solution and fails to filter well under traditional processing conditions. Because of these failures, work was conducted to modify the filtration characteristics of this polysaccharide. Studies were therefore conducted to identify means for improving the filterability of serotype 3 polysaccharide solutions.

Using pH as a variable, an initial study of the impact of pH on protein removal and subsequent filterability of serotype 3 lysate solutions across 25 mm diameter 0.45 μm HT Tuffryn® syringe filters (Pall Life Sciences, Anne Arbor, Mich.) was conducted in the laboratory. Prior to centrifugation, samples of fermentation lysates of serotype 3 were pH-adjusted to 6.6 (two experimental runs), 5.0 (two experimental runs), or 3.0 (one experimental run) using either acetic acid or sulfuric acid in an attempt to remove soluble protein. Lysates were centrifuged and aliquoted into Falcon™ tubes (BD Biosciences, Bedford, Mass.) in one of four conditions in which pH was adjusted using 3N NaOH (sodium hydroxide solution) as follows: 1) control (no pH-adjustment); 2) pH-adjustment to 7.0; 3) pH-adjustment to 8.0; and 4) pH-adjustment to 9.0. Centrates were then pushed through the 0.45 μm syringe filters with relative force required to filter about 3 mL of material.

Figure 7:
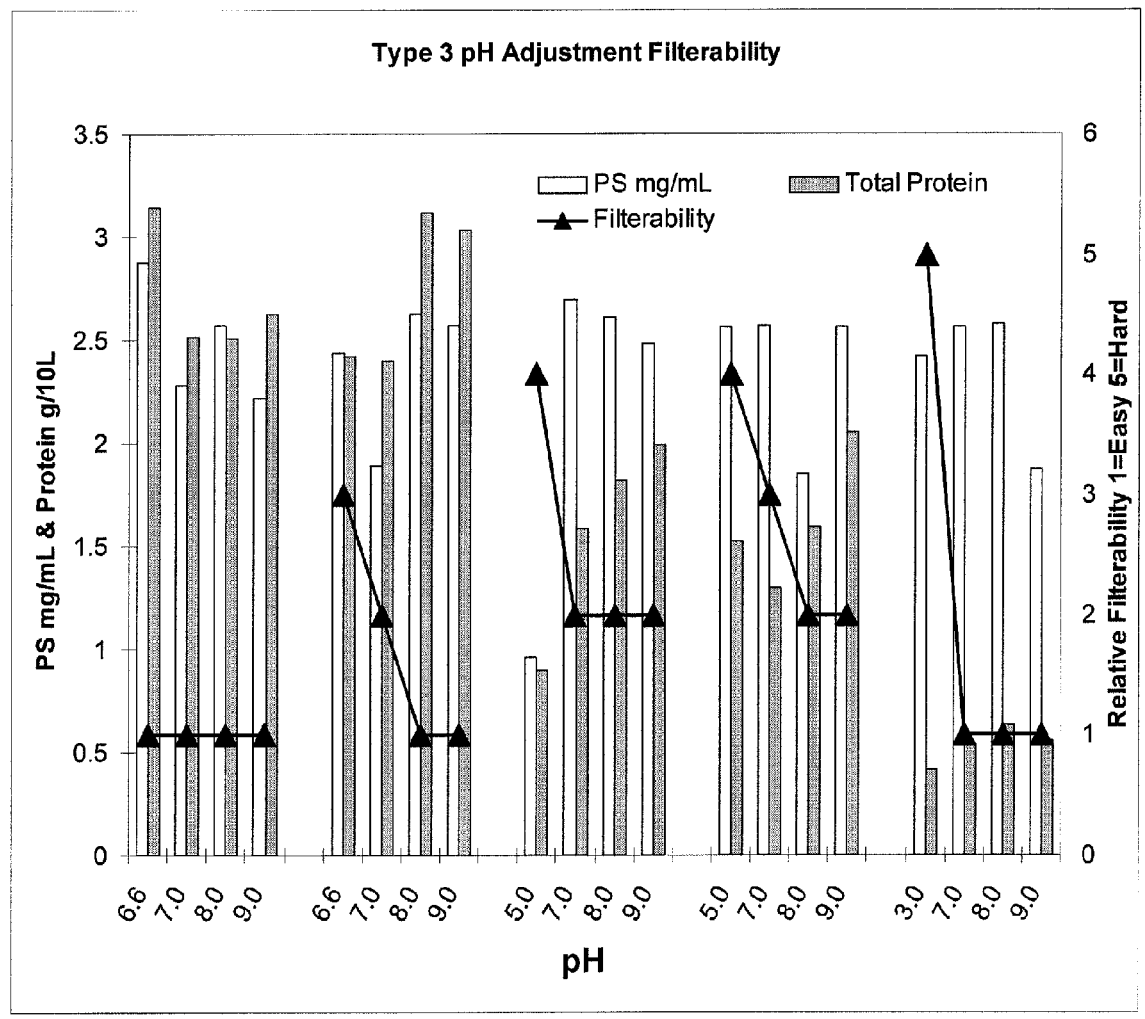
FIG. 7 shows a graph of polysaccharide (PS) concentration, protein concentration, and relative filterability of serotype 3 centrates as a function of centrate pH. Five groups of bar graphs corresponding to five experimental runs are shown. Polysaccharide concentration (mg/mL) and protein concentration (g/10 L) values are provided on the left y-axis. Relative filterability values are provided on the right y-axis, which correspond to the relative force required to push about 3 mL of the serotype 3 centrate through a 0.45 µm syringe filter on a scale of 1 to 5 (1=Easy, 5=Hard).

Results from the five experimental runs described above are shown in FIG. 7, which shows a graph of polysaccharide (PS) concentration, protein concentration, and relative filterability of serotype 3 centrates as a function of centrate pH. Polysaccharide concentration (mg/mL) and protein concentration (g/10 L) values are provided on the left y-axis. Relative filterability values are provided on the right y-axis, which correspond to the relative force required to push about 3 mL of the serotype 3 centrate through a 0.45 μm syringe filter on a scale of 1 to 5 (1=Easy, 5=Hard). As shown in FIG. 7, higher pH levels in all but one of the experimental runs were associated with improved centrate filterability. The results shown in FIG. 7 also demonstrated that very low pH of 3.0 could successfully remove protein but was associated with increased difficulty in filtration.

Figure 8:
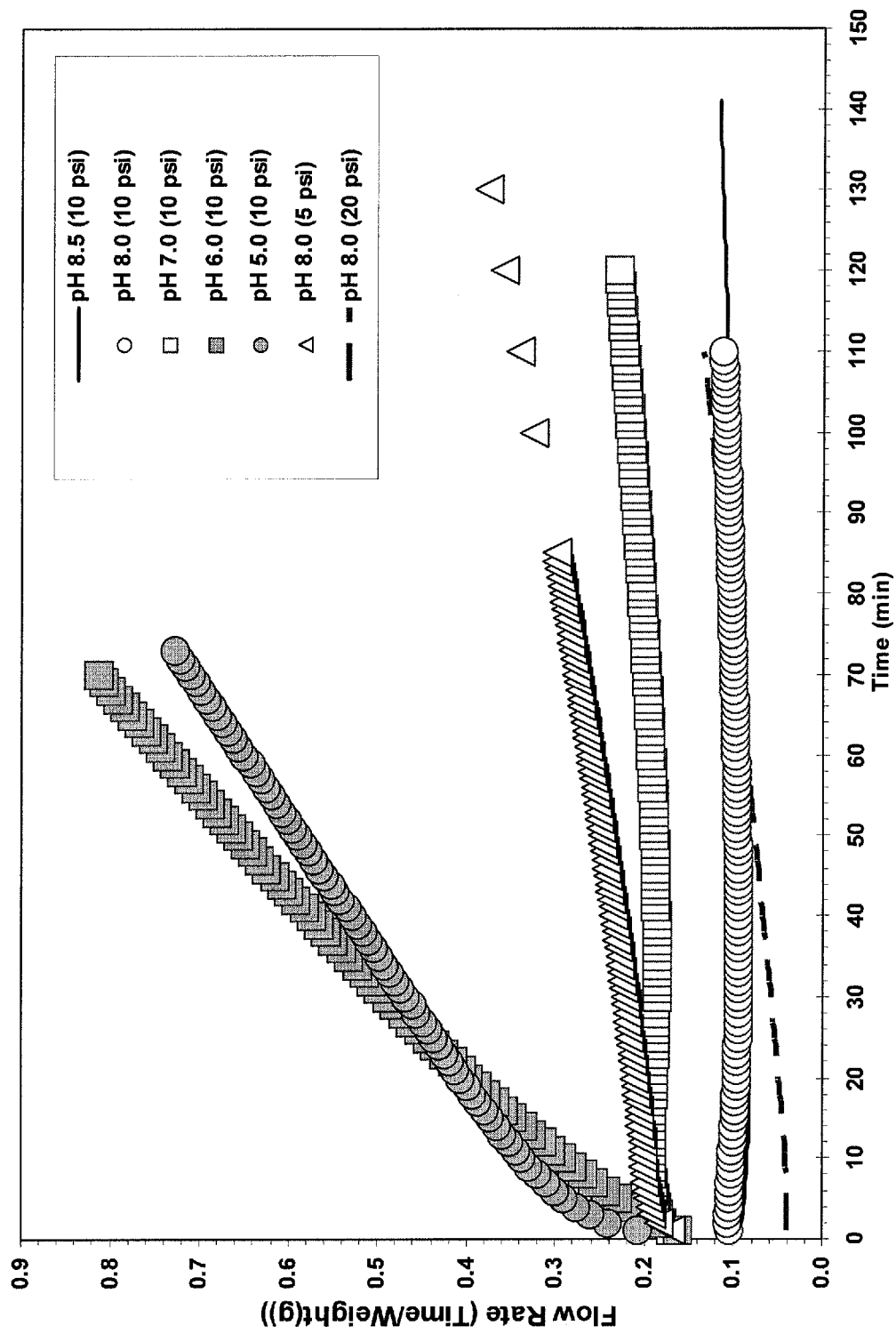
FIG. 8 shows a graph comparing the flow rate over time of serotype 3 centrate samples through depth filters as a function of centrate pH. Flow rate (y-axis) was measured by calculating a ratio for each minute of filtration in which the time in minutes was divided by the total weight in grams of centrate that had passed through the filter at that minute (the lower the ratio, the higher the flow rate). Centrate samples were adjusted to different pH levels (5.0 to 8.5) and pushed through the filters under different constant pressure conditions (5 to 20 pounds per square inch (psi)).

With the impact of pH identified, a controlled laboratory study to determine the impact of pH on filtration capacity was then conducted. Post-centrate material was obtained from a pilot plant run and re-centrifuged in the laboratory. The lysate was divided and pH-adjusted from a range of 5.0 to 8.5. The lysate was placed in a pressure vessel to which a constant pressure was applied. The lysate was passed through tubing over a CUNO 60SP depth filter (CUNO Inc., Meriden, Conn.) and the capacity of the filter analyzed. This was performed for each pH tested (5.0 to 8.5) and under different constant pressure conditions (5 to 20 pounds per square inch (psi)). Results are shown in FIG. 8, which compares the flow rate over time of serotype 3 centrate samples through depth filters as a function of centrate pH. Flow rate (y-axis) was measured by calculating a ratio for each minute of filtration in which the time in minutes was divided by the total weight in grams of centrate that had passed through the filter at that minute (the lower the ratio, the faster the flow rate). As shown in FIG. 8, processing at elevated pH of 7.0 to 8.5 resulted in faster flow rates as compared to processing at lower pH of 5.0 or 6.0 under the same constant pressure condition (10 psi). At a pH of 8.0, a constant pressure of 10 psi or 20 psi was also associated with faster flow rate as compared to 5 psi.

Pilot scale runs incorporating the pH adjustment step described above were then conducted (pilot scale runs listed below in Table 2). Seed bottles containing the *Streptococcus pneumoniae* Type 3 inoculum were grown in fermentors. The cells were chemically lysed and the lysate either centrifuged or heat treated prior to centrifugation. Following centrifugation, the pH was adjusted (except for run IPPPN3-015) and the lysate filtered through depth and 0.45 μm membrane filters prior to being sent downstream for purification. The number of filters required to process lysates from various runs was used as a measure of filterability (the lower the filterability, the more frequent the clogging of filters and the higher the number of filters required to process the lysates). Table 2 shows that only one depth and one membrane filter were required to process lysates from various runs adjusted to a different pH of 7.5 or higher, with or without heat treatment. With run -015, the impact of a pH of 6.6 on filterability was assessed. As shown, for run -015 three filter sets were required for processing of only 37 L. This result was obtained even in the presence of a heating step for protein removal within run -015. After adjusting the remaining lysate material from run -015 to pH 8.2, one set of filters processed the remaining 68 L.

TABLE 2

Filterability of pH-Adjusted Lysates at Pilot Scale

| Run | pH | Volume | Depth Filters | Membrane Filters | Heat Temp °C. | Heat Ramp Up/Hold/Cool Down Time (min) |
|---|---|---|---|---|---|---|
| IPPPN3-001 | 8.0 | 82 L | 1 | 1 | N/A | N/A |
| IPPPN3-003 | 7.5 | 80 L | 1 | 1 | N/A | N/A |
| IPPPN3-004 | 9.0 | 90 L | 1 | 1 | N/A | N/A |
| IPPPN3-006 | 8.5 | 85 L | 1 | 1 | N/A | N/A |
| IPPPN3-007 | 8.5 | 96 L | 1 | 1 | N/A | N/A |
| IPPPN3-010 | 8.0 | 88 L | 1 | 1 | N/A | N/A |
| IPPPN3-011* | 8.2 | 85 L | 1 | 1 | 60 | 42/30/43 |
| IPPPN3-012* | 8.2 | 86 L | 1 | 1 | 70 | 55/50/45 |
| IPPPN3-013 | 8.1 | 90 L | 1 | 1 | N/A | N/A |
| IPPPN3-014* | 8.2 | 103 L | 1 | 1 | 65 | 52/40/51 |
| IPPPN3-015* | 6.6 | 37 L | 3 | 3 | 65 | 57/40/52 |
| IPPPN3-015* | 8.2 | 68 L | 1 | 1 | 65 | 57/40/52 |
| IPPPN3-016* | 8.2 | 87 L | 1 | 1 | 65 | 53/40/43 |

*Lysate heat-treated prior to centrifugation.

Based on laboratory data presented in FIG. 7 and FIG. 8 and the pH adjustment capabilities of the pilot plant facilities, a preferred pH range of 8.2±0.2 was identified for process operation to improve filterability of serotype 3 lysates.

The article "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, certain changes and modifications may be practiced within the scope of the appended claims.

What is claimed is:

1. A method for the reduction or removal of protein impurities from a cellular *Streptococcus pneumoniae* lysate comprising serotype 3 polysaccharides comprising the steps of:
   a) heating said lysate to at least 60° C. for at least 30 minutes to cause protein aggregation and precipitation; and
   b) separating precipitants from said lysate by filtration or centrifugation; wherein a substantially purified serotype 3 polysaccharide-containing lysate is produced.

2. The method of claim 1, wherein step a) comprises heating said lysate to about 60° C. to about 70° C.

3. The method of claim 2, wherein step a) comprises heating said lysate for about 30 to about 50 minutes.

4. The method of claim 3, wherein step a) comprises heating said lysate to about 65° C. for about 40 minutes.

5. The method of claim 1, wherein step a) further comprises heating said lysate to about 60° C. for about 40 minutes.

6. A method for the reduction or removal of protein impurities from a cellular *Streptococcus pneumoniae* lysate comprising serotype 3 polysaccharides comprising the steps of:
   a) heating said lysate to at least 60° C. for at least 30 minutes to cause protein aggregation and precipitation;
   b) centrifuging said lysate and separating precipitated proteins from said lysate to produce a centrate;
   c) increasing the pH of said centrate to at least 8.0; and
   d) filtering said centrate;
   wherein a substantially purified serotype 3 polysaccharide-containing centrate is produced.

7. The method of claim 6, wherein step a) comprises heating said lysate to about 60° C. to about 70° C.

8. The method of claim 6, wherein step a) comprises heating said lysate for about 30 to about 50 minutes.

9. The method of claim 6, wherein step a) comprises heating said lysate to about 65° C. for about 40 minutes.

10. The method of claim 6, wherein step c) comprises increasing the pH of said centrate to between about 8.0 to about 8.4.

11. The method of claim 10, wherein step c) comprises increasing the pH of said centrate to about 8.2.

12. The method of claim 6, wherein step d) comprises filtering said centrate using at least one filter selected from the group consisting of a membrane filter and a depth filter.

13. The method of claim 12, wherein said membrane filter is a 0.45 μm pore size membrane filter.

14. The method of claim 6, where step a) further comprises heating said lysate to about 60° C. for about 40 minutes.

* * * * *